(12) United States Patent
Schnabel et al.

(10) Patent No.: US 7,057,043 B2
(45) Date of Patent: Jun. 6, 2006

(54) PROCESSES FOR PREPARING AMINOPHENYLSULFONYLUREAS, AND INTERMEDIATES THEREFOR

(75) Inventors: Gerhard Schnabel, Grosswallstadt (DE); Jan Vermehren, Cambridge (GB); Lothar Willms, Hofheim (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 73 days.

(21) Appl. No.: 10/936,180

(22) Filed: Sep. 8, 2004

(65) Prior Publication Data

US 2005/0033047 A1    Feb. 10, 2005

Related U.S. Application Data

(60) Division of application No. 10/288,052, filed on Nov. 5, 2002, now Pat. No. 6,790,955, which is a division of application No. 09/644,201, filed on Sep. 18, 2000, now Pat. No. 6,500,952, which is a continuation of application No. 08/741,613, filed on Oct. 31, 1996, now abandoned.

(30) Foreign Application Priority Data

Nov. 2, 1995    (DE)    ................................ 195 40 701

(51) Int. Cl.
    *C07D 239/02*    (2006.01)
(52) U.S. Cl. .................................................... 544/332
(58) Field of Classification Search ................ 544/211, 544/213, 332
    See application file for complete search history.

(56) References Cited

U.S. PATENT DOCUMENTS

| 3,203,987 | A |   | 8/1965 | Hoefle ........................ 260/556 |
| 4,383,113 | A |   | 5/1983 | Levitt ......................... 544/211 |
| 4,394,506 | A |   | 7/1983 | Levitt ......................... 544/321 |
| 4,892,946 | A |   | 1/1990 | Levitt ......................... 544/321 |
| 4,981,509 | A |   | 1/1991 | Hillemann ...................... 71/93 |
| 5,449,812 | A |   | 9/1995 | Schnabel et al. ............. 560/13 |
| 5,922,646 | A | * | 7/1999 | Schnabel et al. ........... 504/214 |

FOREIGN PATENT DOCUMENTS

| DE | 4236902      | 5/1994  |
| EP | 0 001 515    | 4/1979  |
| EP | 0 007 687    | 2/1980  |
| EP | 0 030 138    | 6/1981  |
| EP | 0 116 518    | 8/1984  |
| EP | 0 330 201    | 8/1989  |
| EP | 0 559 044    | 9/1993  |
| WO | WO 94/10154  | 5/1994  |
| WO | WO 95 29899  | 11/1995 |

OTHER PUBLICATIONS

Hovius et al, Tetrahedron Letters, "Intramolecular Sulfonmide-Carboxamide Rearrangement", vol. 24, No. 30, (1983), pp. 3137-3140.

G. Cohn "Die Organishen Geschmackstoffe", Siemenroth, Berlin, Germany, pp. 708-720, (1914).
Hovius et al, "Intramolecular Sulfonamide-Carboxamide of Nitro-Substituted 1,2-Benzothiazol-3(2H)-one-1-dioxides (Nitrosaccharins" Heterocyclic Chem. vol. 23, pp. 1253-1255 (1986).

* cited by examiner

*Primary Examiner*—James O. Wilson
*Assistant Examiner*—Zachary C. Tucker
(74) *Attorney, Agent, or Firm*—Frommer Lawrence & Haug LLP

(57) ABSTRACT

The invention relates to the preparation of compounds (I)

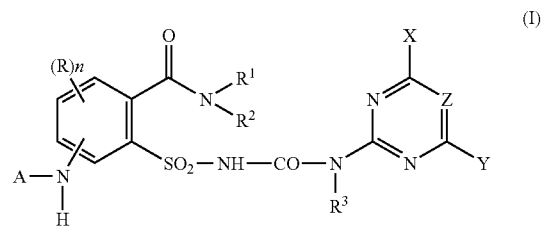

in which A=H or acyl and $R^1$, $R^2$, $R^3$, R, n, X, Y and Z are as defined in claim 1 by halogenation and rearrangement of compounds (II) (optionally salt) to give compounds (III)

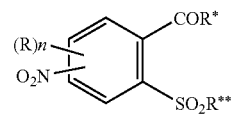

$R^*$=OH, $R^{**}$=$NR^1R^2$    (II)

$R^*$=$NR^1R^2$, $R^{**}$=Cl    (III)

$R^*$=$NR^1R^2$, $R^{**}$=$NH_2$    (IV)

a) ammonolysis of (III) to (IV), reduction of the nitro group and reaction with carbamate (salts) (VI) of the formula Ar—OCO—N(M)-Het, where Ar=phenyl, M=H or cation and Het=heterocycle from formula (I), to give compounds (I) (A=H), or
b) ammonolysis of (III) to (IV), reaction with carbamate (salt) (VI) and reduction of resulting compounds (VII) at the $NO_2$ group to give compounds (I) (A=H), or
c) reaction of (III) with cyanates and amines (V) of the formula $HNR^{3-}$Het and reduction of the resulting compound (VII) at the $NO_2$ group to give compounds (I) (A=H) and optional acylation if A is to be other than H. Compounds of the formulae (I) (A=H), (III), (IV), (V), (VI) (M=cation) and (VII) are novel.

4 Claims, No Drawings

PROCESSES FOR PREPARING AMINOPHENYLSULFONYLUREAS, AND INTERMEDIATES THEREFOR

RELATED APPLICATIONS

This application is a divisional of application U.S. Ser. No 10/288,052, filed Nov. 5, 2002 and now allowed and set to issue as U.S. Pat. No. 6,790,955 on Sep. 14, 2004, which in turn is a divisional of application U.S. Ser. No. 09/644,201, filed on Sep. 18, 2000 and issued as U.S. Pat. No. 6,500,952 on Dec. 31, 2002, herein incorporated by reference, which in turn is a continuation of application U.S. Ser. No. 08/741,613, filed Oct. 31, 1996 and abandoned, herein incorporated by reference, which in turn claims priority to German application Ser. No.195 40 701.6, filed Nov. 2, 1995.

The invention concerns the technical field of processes for preparing herbicides or plant growth regulators.

It is known that heterocyclically substituted phenylsulfonylureas which carry an amino group or a functionalized amino group on the phenyl ring possess herbicidal and plant growth-regulatory properties (EP-A-1515; EP-A-7687 (=U.S. Pat. No. 4,383,113); EP-A-30138 (=U.S. Pat. No. 4,394,506); U.S. Pat. No. 4,892,946; U.S. Pat. No. 4,981,509; EP-A-116518 (=U.S. Pat. No. 4,664,695, U.S. Pat. No. 4,632,695)), WO-94/10154. In addition, German Patent Application P 4415049.0 (WO 95/29899) has proposed acylaminosulfonylureas as herbicides. The cited literature includes descriptions of processes for preparing sulfonylureas. The compounds having a free amino group on the phenyl ring are themselves herbicidal active ingredients or are suitable as starting compounds for preparing compounds with a substituted amino group.

Owing to the large number of reactive functional groups in the molecule, the methods for preparing aminophenylsulfonylureas can often be carried out only with low yields or poor purities. Another disadvantage is that many processes are based on the use of protecting groups, for example the tert-butyl group in the case of sulfonamides, whose elimination requires specific and difficult-to-handle reagents, such as trifluoroacetic acid. Moreover, the majority of the known processes for preparing sulfonylurea compounds are multistage and therefore give only a moderate overall yield, as a rule.

The object of the invention is therefore the provision of a process which is suitable for preparing a relatively large group of herbicides from the aminophenylsulfonylurea series and which avoids many of the abovementioned disadvantages.

The invention provides a process for preparing compounds of the formula (I) and salts thereof,

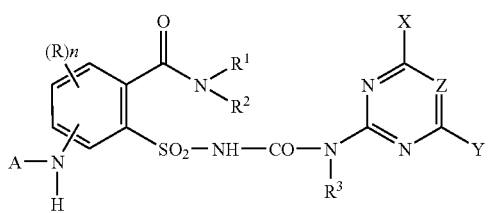

in which $(R)_n$ is n identical or different radicals from the group consisting of halogen, alkyl and alkoxy, n is 0, 1, 2 or 3, preferably 0 or 1, especially 0, A is hydrogen or an acyl radical, $R^1$ is hydrogen or an unsubstituted or substituted hydrocarbon or hydrocarbonoxy radical having 1 to 6 carbon atoms, preferably 1 to 4 carbon atoms, $R^2$ is hydrogen or an unsubstituted or substituted hydrocarbon radical having a total of 1 to 10 carbon atoms, preferably 1 to 4 carbon atoms, or the group $NR^1, R^2$ is a heterocyclic ring having 3 to 8 ring atoms which is unsubstituted or substituted and contains the nitrogen atom of the group $NR^1R^2$ as ring heteroatom and may also contain one or two further ring heteroatoms from the group consisting of N, O and S, $R^3$ is hydrogen or $C_1$–$C_4$-alkyl, X and Y independently of one another are halogen, $C_1$–$C_6$-alkyl, $C_1$–$C_6$-alkoxy, $C_1$–$C_6$-alkylthio, each of the three latter radicals being unsubstituted or substituted by one or more radicals from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, and Z is CH or N, which comprises 1. (Stage 1) reacting the compound of the formula (II)

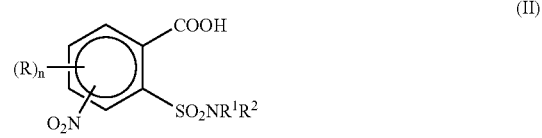

or its salts in the presence of a halogenating agent, with formation of the carbonyl halide and its rearrangement to form the compound of the formula (III)

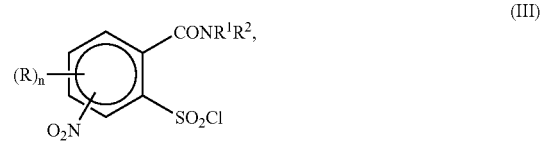

2. (Stage 2) then
a) subjecting the compound (III) to ammonolysis at the $SO_2Cl$ group to give the compound of the formula (IV)

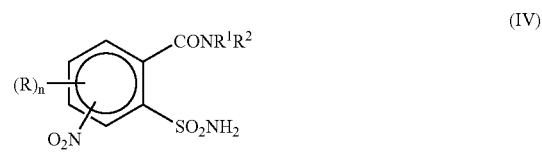

then reducing the compound (IV) at the nitro group to give the compound (V)

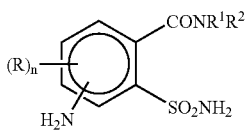

and then reacting the compound (V) with the carbamate or carbamate salt of the formula (VI)

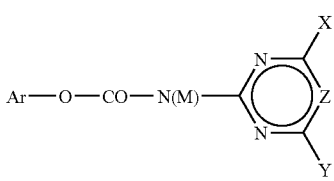

in which Ar is unsubstituted or substituted phenyl and M is H, $C_1$–$C_4$-alkyl or a metal cation, to give the compound of the formula. (I) in which $R^3$ is, in agreement with M in formula (VI), H or $C_1$–$C_4$-alkyl or, if M is a metal cation, $R^3$ is a hydrogen atom, and A=H, or b) subjecting the compound of the formula (III) to ammonolysis at the $SO_2Cl$ group to give the abovementioned compound of the formula (IV), then reacting the compound (IV) with the carbamate or carbamate salt of the abovementioned formula (VI) to give the compound of the formula (VII)

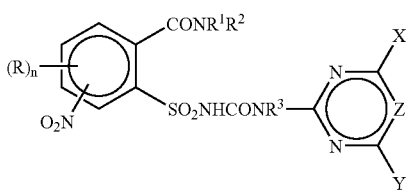

in which $R^3$ is, in agreement with M in formula (VI), either H or $C_1$–$C_4$-alkyl or, if M is a metal cation, is a hydrogen atom, and reducing the compound of the formula (VII) at the nitro group to give the compound of the formula (I) in which A is H, or c) reacting the compound of the formula (III) with cyanates and with the heterocyclic amine of the formula (VIII)

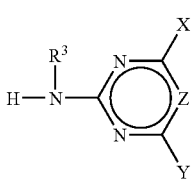

in which $R^3$ is as defined in formula (I) to give the sulfonylurea of the formula (VII), which by reduction at the nitro group gives the compounds of the formula (I) in which A is H, and 3. (Stage 3) if A in the end product of the formula (I) is not hydrogen but is an acyl radical, acylating the compound of the formula (I) obtained in Stage 2, in which A is H, the radicals $(R)_n$, $R^1$, $R^2$, X, Y, and Z in the formulae (II) to (VIII) being as defined for the end product of the formula (I).

In the formulae (I) to (VIII) and in the formulae used below, the radicals alkyl, alkoxy, haloalkyl, haloalkoxy, alkylamino and alkylthio and their unsaturated and/or substituted counterparts may in each case be straight-chain or branched in the carbon framework. Unless indicated specifically, preference is given in the case of these radicals to the lower carbon frameworks, e.g. those having 1 to 4 carbon atoms, or, in the case of unsaturated groups, having 2 to 4 carbon atoms. Alkyl radicals, both alone and in the composite definitions such as alkoxy, haloalkyl, etc., are for example methyl, ethyl, n-propyl, isopropyl, n-butyl isobutyl, tert-butyl or 2-butyl, pentyls, hexyls, such as n-hexyl, isohexyl and 1,3-dimethylbutyl, and heptyls, such as n-heptyl, 1-methylhexyl and 1,4-dimethylpentyl; alkenyl and alkynyl radicals have the meaning of the possible unsaturated radicals corresponding to the alkyl radicals; alkenyl is for example allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is for example propargyl, but-2-yn-1-yl; but-3-yn-1-yl, 1-methylbut-3-yn-1-yl.

Halogen is for example fluorine, chlorine, bromine or iodine. Haloalkyl, haloalkenyl and haloalkynyl are alkyl, alkenyl and, respectively, alkynyl which are partially or completely substituted by halogen, preferably by fluorine, chlorine and/or bromine, in particular by fluorine or chlorine, examples being $CF_3$, $CHF_2$, $CH_2F$, $CF_3CF_2$, $CH_2FCHCl$, $CCl_3$, $CHCl_2$, $CH_2CH_2Cl$; haloalkoxy is for example $OCF_3$, $OCHF_2$, $OCH_2F$, $CF_3CF_2O$, $OCH_2CF_3$ and $OCH_2CH_2Cl$; corresponding comments apply to haloalkenyl and other halogen-substituted radicals.

A hydrocarbon radical is a straight-chain, branched orcyclic and saturated or unsaturated aliphatic or aromatic hydrocarbon radical, for example alkyl, alkenyl, alkynyl, cycloalkyl, cycloalkenyl or aryl, preferably alkyl, alkenyl or alkynyl having up to 12 carbon atoms or cycloalkyl having 5 or 6 ring atoms, or phenyl; corresponding comments apply to a hydrocarbonoxy radical.

A heterocyclic radical or ring can be saturated, unsaturated or heteroaromatic; it contains one or more ring heteroatoms, preferably from the group consisting of N, O and S; it preferably has 5 or 6 members and contains 1, 2 or 3 ring heteroatoms. The radical may for example be a heteroaromatic radical or ring as defined above, or is a partially hydrogenated radical such as oxiranyl, pyrrolidinyl, piperidyl, piperazinyl, dioxolanyl, morpholinyl, and tetrahydrofuryl. Suitable substituents for a substituted heterocyclic radical are those mentioned below, and also oxo. The oxo group may also be on the ring heteroatoms, which may exist in various oxidation states in the case, for example, of N and S.

Substituted radicals, such as substituted hydrocarbon radicals, e.g. substituted alkyl, alkenyl, alkynyl, aryl, phenyl and benzyl or substituted heteroaryl, a substituted bicyclic radical or ring or a substituted bicyclic radical, with or without aromatic components, are for example a substituted radical derived from the unsubstituted parent structure, the substituents being for example one or more, preferably 1, 2 or 3, radicals from the group consisting of halogen, alkoxy, haloalkoxy, alkylthio, hydroxyl, amino, nitro, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl and unsaturated aliphatic radicals corresponding to the saturated hydrocarbon-containing radicals mentioned, such as alkenyl, alkynyl, alkenyloxy, alkynyloxy, etc. In the case of radicals containing carbon atoms, preference is given to those having 1 to 4 carbon atoms, especially 1 or 2 carbon atoms. In general, preference is given to substituents from the group consisting of halogen, e.g. fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano. In this context, the substituents methyl, methoxy and chlorine are particularly preferred.

Substituted or unsubstituted phenyl is preferably phenyl which is unsubstituted or is substituted one or more times, preferably up to three times, by identical or different radicals from the group consisting of halogen, $C_1$–$C_4$-alkyl, $C_1$–$C_4$-alkoxy, $C_1$–$C_4$-haloalkyl, $C_1$–$C_4$-haloalkoxy and nitro, examples being o-, m- and p-tolyl, dimethylphenyls, 2-, 3- and 4-chlorophenyl, 2-, 3- and 4-trifluoro- and -trichlorophenyl, 2,4-, 3,5-2,5- and 2,3-dichlorophenyl, and o-, m- and p-methoxyphenyl.

An acyl radical is the radical of an organic acid, for example the radical of a carboxylic acid, and radicals of acids derived therefrom, such as of thiocarboxylic acid, of unsubstituted or N-substituted iminocarboxylic acid, or is a radical of carbonic acid monoesters, of unsubstituted or N-substituted carbamic acid, sulfonic acids, sulfinic acids, phosphonic acids, phosphinic acids. Acyl is for example formyl, alkylcarbonyl such as ($C_1$–$C_4$-alkyl)-carbonyl, phenylcarbonyl, where the phenyl ring can be substituted, for example, as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

There is particular interest in novel processes for preparing compounds of the formula (I) or salts thereof in which
$(R)_n$ is n identical or different radicals from the group consisting of halogen, $C_1$–$C_4$-alkyl and $C_1$–$C_4$-alkoxy,
n is 0 or 1, especially 0,
A is H or acyl having 1 to 8 carbon atoms, especially 14 carbon atoms,
$R^1$ is H, $C_1$–$C_6$-alkyl, $C_2$–$C_6$-alkenyl, $C_2$–$C_6$-alkynyl, $C_1$–$C_6$-alkoxy, $C_2$–$C_6$-alkenoxy, $C_2$–$C_6$-alkynoxy or $C_5$–$C_6$-cycloalkyl, each of the 7 latter radicals being unsubstituted or substituted by one or more radicals from the group consisting of halogen, $C_1$–$C_4$-alkoxy, $C_1$–$C_4$-haloalkoxy, $C_1$–$C_4$-alkylthio, mono- and di-($C_1$–$C_4$-alkyl)-amino, cyano, azido, formyl, ($C_1$–$C_4$-alkyl)-carbonyl, ($C_1$–$C_4$-alkoxy)-carbonyl, $C_1$–$C_4$-alkylsulfinyl and $C_1$–$C_4$-alkylsulfonyl, or is phenyl which is unsubstituted or substituted by radicals from the group consisting of halogen, $C_1$–$C_4$-alkyl, $C_1$–$C_4$-alkoxy, $C_1$–$C_4$-haloalkyl, $C_1$–$C_4$-haloalkoxy and nitro,
$R^2$ is H, $C_1$–$C_6$-alkyl, $C_2$–$C_6$-alkenyl or $C_2$–$C_6$-alkynyl, each of the three latter radicals being unsubstituted or substituted by one or more radicals from the group consisting of halogen, $C_1$–$C_4$-alkoxy, $C_1$–$C_4$-haloalkoxy, $C_1$–$C_4$-alkylthio, mono- and di-($C_1$–$C_4$-alkyl)-amino, cyano, azido, formyl, ($C_1$–$C_4$-alkyl)-carbonyl, ($C_1$–$C_4$-alkoxy)-carbonyl, $C_1$–$C_4$-alkylsulfinyl and $C_1$–$C_4$-alkylsulfonyl, or the group
$NR^1R^2$ is a heterocyclic ring of 4, 5 or 6 ring atoms which may contain up to two further ring heteroatoms from the group consisting of N and O in the ring and which is unsubstituted or substituted by one or more radicals from the group consisting of $C_1$–$C_4$-alkyl,
$R^3$ is H or $CH_3$,
one of the radicals X and Y
is halogen, $C_1$–$C_2$-alkyl $C_1$–$C_2$-alkoxy, $C_1$–$C_2$-alkylthio, each of the three latter radicals being unsubstituted or substituted by one or more radicals from the group consisting of halogen, $C_1$–$C_2$-alkoxy and $C_1$–$C_2$-alkylthio, or is mono- or di-($C_1$–$C_2$-alkyl)amino, preferably halogen, methyl or methoxy, and
the other of the radicals X and Y
is $C_1$–$C_2$-alkyl, $C_1$–$C_2$-haloalkyl, $C_1$–$C_2$-alkoxy, $C_1$–$C_2$-haloalkoxy or $C_1$–$C_2$-alkylthio, preferably methyl or methoxy, and
Z is CH or N, preferably CH.

Preference is also given to novel processes for preparing compounds of the formula (I) or salts thereof in which
A is hydrogen, formyl, ($C_1$–$C_4$-alkyl)-carbonyl, which is unsubstituted or substituted by one or more radicals from the group consisting of halogen and ($C_1$–$C_4$)-alkoxy,
or is ($C_1$–$C_4$-alkoxy)-carbonyl, phenoxycarbonyl, phenylcarbonyl, phenyl-($C_1$–$C_4$-alkyl)-carbonyl or phenyl-($C_1$–$C_4$-alkoxy)-carbonyl, where the phenyl in each of the 4 latter radicals is unsubstituted or substituted, A preferably being formyl, acetyl, propionyl, methoxycarbonyl, ethoxycarbonyl, benzoyl or benzyloxycarbonyl, especially formyl, ($C_1$–$C_4$-alkyl)-carbonyl or ($C_1$–$C_4$-alkoxy)-carbonyl.

Preference is given to novel processes for preparing compounds of the formula (I) or salts thereof in which
$R^1$ is H, $C_1$–$C_2$-alkyl, $C_1$–$C_2$-alkoxy, phenyl which is unsubstituted or substituted by one or more radicals from the group consisting of halogen, $C_1$–$C_2$-alkyl, $C_1$–$C_2$-alkoxy, $C_1$–$C_2$-haloalkyl and $C_1$–$C_2$-haloalkoxy, especially methyl or ethyl,
$R^2$ is H or $C_1$–$C_2$-alkyl, especially methyl or ethyl, or the group
$NR^1R^2$ is a heterocyclic ring of 5 or 6 ring atoms which may contain up to one further ring heteroatom from the group consisting of N and O in the ring and which is unsubstituted or substituted by one or more $C_1$–$C_2$-alkyl radicals, especially pyrrolidinyl or piperidyl,
$R^3$ is H or $CH_3$, especially H.

Among the novel processes, preference is given to those in which in the compounds of the formula (I) the group of the formula $NH_2$ on the phenyl radical is para to the group CO—$NR^1R^2$ and meta to the $SO_2$ group.

The invention additionally provides the novel individual stages of the overall process, and the novel intermediates thereof, especially Stage 1 and Stages 2a and 2b, to the extent that it relates to the reaction with carbamate salts (VI) in which M is a cation.

The reaction of compounds (II) to compounds (III) can be accomplished with customary halogenating agents for the preparation of carbonyl chlorides, for example with thionyl chloride or thionyl bromide. For this purpose the nitro-ortho-sulfamoyl benzoic acid (II) is reacted with an excess of halogenating agent in an aprotic organic solvent and is then heated to a temperature at which the rearrangement reaction takes place. Suitable organic solvents are aprotic organic solvents which are inert with respect to the reactants (referred to as inert solvents) and whose boiling point is above the temperature required for the rearrangement reaction. The reactants may for example be reacted homogeneously or in a heterogeneous mixture, (for example in suspension) to give the desired products. For example, the reaction can be carried out in halogenated or unhalogenated aromatic hydrocarbons, such as toluene, xylene, chlorobenzene or chlorotoluene. The reaction temperatures for this halogenation are from about 50 to 100° C. and for the rearrangement are from over 100° C. to the boiling point of the aprotic solvent, for example from 110 to 160° C.; in some cases rearrangement takes place to an inadequate extent even at lower temperatures, for example at 70° C. The thionyl chloride can be used in equimolar quantities or in an excess relative to one mole of the benzoic acid. Instead of the benzoic acid derivatives it is also possible to react the corresponding salts, for example the alkali metal or alkaline earth metal salts (e.g. Na, K. Li, Mg and Ca salts), with a halogenating agent, for example thionyl chloride, to give the corresponding 2-chlorosulfonylbenzamide derivatives (III).

It is already known to react 2-(N,N-dialkyl-aminosulfonyl)-benzoic acids which are unsubstituted or carry simple alkyl groups on the phenyl ring with a fourfold to eightfold excess of thionyl chloride or thionyl bromide in benzene, dichloromethane or chloroform at room temperature (25° C.) to give N,N-dialkyl-2-(chloro- or, respectively, -bromosulfonyl) benzamides; see K. Hovius et al., Tetrahedron Lett. 1983, 3137–3140. The corresponding reaction of the N,N-dialkyl-o-sulfamoylnitrobenzoic acids (II) was not hitherto known and did not take place under these conditions. Only by modification of the known conditions with respect to temperature and solvent does the reaction proceed with the tested nitrobenzoic acids (II) as well.

The required compounds of the formula (II) can be prepared by alternative methods. For instance, the oxidation of the methyl group of compounds of the formula (IX)

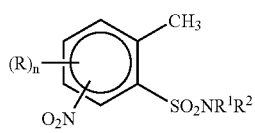

(IX)

leads to the compound of the formula (II). The oxidation can be carried out, for example, by methods similar to known methods for the preparation of benzoic acids from toluenes. The toluene derivative of the formula (IX) can be obtained by reacting the sulfochloride of the formula (X) with an amine of the formula $HNR^1R^2$:

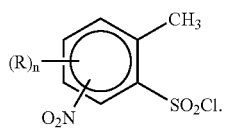

(X)

A further method of obtaining compound (II) is the ammonolysis of the sulfochloride (XI)

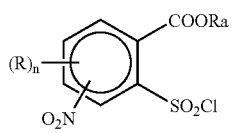

(XI)

in which Ra is an alkyl radical such as methyl or ethyl with an amine of the formula $HNR^1R^2$ to give the sulfonamide, followed by hydrolysis of the resulting compound at the carboxylic ester group. The individual reactions can be carried out in analogy with known methods of the same type. For example, the ester functions can be hydrolyzed using alkali metal hydroxides or alkaline earth metal hydroxides, such as LiOH, NaOH, KOH, $Mg(OH)_2$, $Ca(OH)_2$ for example, in various polar solvents, for example, methanol, ethanol, isopropanol, chlorobenzene, chlorotoluene, tetrahydrofuran, 1,2-dimethoxyethane (DME), diglyme, dimethylformamide (DMF), N,N-dimethylacetamide (DMA), N-methylpyrrolidone (NMP) or water, or solvent mixtures of suitable solvents, at temperatures, for example, between −20° C. and 150° C., preferably between −10° C. and 100° C.

The sulfonamides of the formula (IV) can be obtained in high yields by reacting the sulfochlorides (III) with ammonia (ammonolysis). The reaction can generally be carried out at temperatures from −20° C. to 150° C., preferably from −10° C. to 100° C. Suitable solvents are organic solvents inert under the reaction conditions, for example dipolar aprotic solvents such as DMF, DMA, NMP, acetonitrile,
ethers such as tert-butyl methyl ether, dimethoxyethane (DME), THF, diethyl ether, diisopropyl ether,
esters such as ethyl acetate, butyl acetate,
chlorinated or unsubstituted hydrocarbons such as toluene, o-chlorotoluene, chlorobenzene,
alcohols such as methanol, ethanol, isopropanol,
water, or
mixtures of inert solvents.

Particularly preferred solvents are nitriles such as acetonitrile, ethers such as diethyl ether, tert-butyl methyl ether, THF or dimethoxyethane (DME), or esters such as ethyl acetate and butyl acetate, or chlorinated or unsubstituted hydrocarbons such as toluene, chlorobenzene and chlorotoluene.

The reduction of the nitro group in compounds of the formula (IV) can be carried out, for example, by catalytic hydrogenation (Stage 2, section a). A host of common commercial catalysts are suitable for the hydrogenation, examples being platinum, palladium or Raney nickel, and can be used in analogy to standard techniques. Examples of suitable organic and inorganic solvents which are inert under the reaction conditions are dipolar aprotic solvents such-as DMA, DMF, NMP or $CH_3CN$;
esters such as ethyl acetate or butyl acetate;
ethers such as DME, diglyme, tetraglyme, THF or diethyl ether;
alcohols such as methanol or ethanol;
organic acids such as acetic acid or propionic acid;
water, or
mixtures of suitable inert solvents.

The reaction temperature can be varied, for example, between −20° C. and 150° C., preferably from −10° C. to 100° C. The hydrogen pressure can likewise be varied within wide limits and is, for example, from 1 bar to 200 bar, preferably from 1 bar to 100 bar, in particular from 1 bar to 50 bar.

The reaction of compounds (V) with carbamates of the formula (VI) is intended to take place preferentially and with substantial selectivity at the sulfonamide group rather than at the alternative amino groups on the phenyl radical. If the compound (V) is reacted with carbamates of the formula (IV) in accordance with standard techniques, for example in acetonitrile in the presence of a sterically hindered base such as 1,8-diazabicyclo[5.4.0]undec-7-ene(DBU), then the sulfonamide function and amino function are similar in reactivity, i.e. the chemoselectivity of the reaction is completely unsatisfactory. For example, the reaction of 5-amino-2-dimethylaminocarbonylbenzenesulfonamide with 4,6-dimethoxy-2-phenoxycarbonylaminopyrimidine in the presence of DBU leads to two products in a 2:1 ratio, namely to 5-amino-2-dimethylaminocarbonyl-N-[(4,6-dimethoxypyrimidin-2-yl)aminocarbonyl]benzenesulfonamide and to 5-[(4,6-dimethoxypyrimidin-2-yl)aminocarbonylamino]-2-dimethylaminocarbonyl-N-[(4,6-dimethoxypyrimidin-2-yl)aminocarbonyl]-benzenesulfonamide (byproduct) (see Comparison Example).

However, the reaction can surprisingly be carried out selectively in the case of the reaction with carbamate salts. In accordance with the invention, selectivities which are better, for example, than those of the reaction with carbamates of the formula (XI) in which M is hydrogen are achieved by using carbamate salts (VI), in which M is a cation, for example sodium or potassium salts of the carbamates.

For this reaction, for example, the carbamate (VI) (M=H) is first of all reacted with appropriate bases, for example alkali metal and alkaline earth metal hydroxides such as LiOH, NaOH, KOH, $Mg(OH)_2$, $Ca(OH)_2$ or tetraalkylammonium hydroxides such as tetramethylammonium hydroxide, or alkali metal or alkaline earth metal hydrides, for example NaH, KH, $CaH_2$ or alkali metal or alkaline earth metal alcoholates, such as $NaOCH_3$, $NaOC_2H_5$, sodium isopropylate, sodium tert-butylate, $KOCH_3$, $KOC_2H_5$, potassium isopropylate, potassium tert-butylate, or mixtures of bases in appropriate solvents, to form a salt of the formula (VI) (M=cation). Suitable solvents are inert organic solvents, preferably aprotic apolar or aprotic polar solvents such as ethers (e.g. THF, DME, diethyl ether, diisopropyl ether, dioxane, tert-butylmethyl ether), amides (e.g. DMF, DMA, NMP), nonhalogenated or halogenated aromatic hydrocarbons, such as toluene, chlorotoluene or chlorobenzene.

For alkali metal and alkaline earth metal salts, moreover, further suitable solvents are alcohols such as methanol, ethanol, isopropanol, or solvent mixtures.

For alkali metal, alkaline earth metal and tetraalkylammonium hydroxides, moreover, water is also an appropriate solvent or solvent component. Particular preference is given to ethers, such as THF, DME or dioxane.

The resulting salts of the formula (VI) (M=cation) are advantageously produced in solution and employed without isolation for the subsequent reaction. For this purpose the salts are, for example, reacted in solution with sulfonamides of the formula (V) at temperatures from −40° C. to 150° C., preferably from −40° C. to 80° C., in particular from −20° C. to 80° C. Following acidification of the reaction solution with acids, for example with organic acids such as formic acid or acetic acid, or with mineral acids such as hydrochloric acid or sulfuric acid, the sulfonylureas of the formula (I) (A=H) (=compounds (I')) can be isolated by standard methods. A favorable yield is generally achieved at a molar ratio of sulfonamides (V) to carbamate salt (VI) of from 1:0.7 to 1:1.5.

Preferred variants are the reactions of carbamates of the formula (VI) (M=H) with the hydroxides or alcoholates of alkali metals, for example KOH, $NaOCH_3$, $KOCH_3$, sodium tert-butylate or potassium tert-butylate, sodium isopropylate or potassium isopropylate, especially with the sterically bulky alkali metal alcoholates, in dipolar aprotic solvents such as THF, dioxane, DMF, DMA, especially THF, DME or dioxane.

An alternative route to sulfonylureas (I') (=formula (I) where A=H) is offered by the variant 2b mentioned. According to this variant, the compounds (III) are first of all reacted by ammonolysis, as in step 1 of Stage 2a), to give nitrobenzenesulfonamides of the formula (IV), which are subsequently reacted with carbamates of the formula (VI) in analogy to standard conditions in the presence of bases, for example organic nitrogen bases such as DBU or triethylamine, alkali metal or alkaline earth metal hydroxides, such as LiOH, NaOH, KOH, $Mg(OH)_2$ or $Ca(OH)_2$, alkali metal or alkaline earth metal alcoholates, for example $NaOCH_3$, $KOCH_3$, Na or K isopropylate, Na or K tert-butylate, to form the nitrosulfonylureas of the formula (VII). The ratios of the reactants are preferably from 0.7 to 1.5 equivalents of carbamates (VI) and from 0.7 to 2.2 equivalents of base, based in each case on 1 equivalent of sulfonamide (IV).

The reactions of compounds (IV) to compounds (VII) take place at temperatures of, for example, from −20° C. to 100° C., preferably from −10° C. to about 70° C., in inert organic solvents, for example in aprotic solvents such as ethers (e.g. THF, DME, dioxane, diethyl ether), acetonitrile, DMF, DMA, NMP, alcohols, esters such as ethyl acetate or butyl acetate, chlorinated aliphatic or aromatic hydrocarbons such as difluoromethane, trichloroethane, chlorobenzene or o-chlorotoluene, or protic solvents such as, for example, methanol, ethanol, isopropanol or water, or appropriate solvent mixtures.

The nitrosulfonylureas of the formula (VII) can also be obtained by analogy with the above-described reaction of carbamate salts of the formula (VI) (M=cation) with sulfonamides of the formula (V) to give the sulfonylureas (I') (=formula (I) where A=H), by reaction of sulfonamides of the formula (IV) (M=cation) with carbamate salts (M=cation) (VI).

The nitrosulfonylureas (VII) can subsequently be reacted by catalytic hydrogenation to give the aminosulfonylureas (I') of the formula (I) in which A is H.

The hydrogenation can be carried out in analogy to the above-described hydrogenation of compounds of the formula (IV), in accordance with standard techniques. When an aqueous medium is used as solvent, basic solutions or buffered aqueous solutions having a pH of from 5 to 13, preferably from 7 to 11, are particularly suitable.

Alternatively, instead of the neutral nitrosulfonylureas (VII) their salts can be employed for the hydrogenation.

Examples of suitable cations to partner the sulfonylurea anions of the formula (VII) are alkali metal or alkaline earth metal cations, for example $Li^+$, $Na^+$, $K^+$, $Cs^+$, $Mg^{2+}$, $Ca^{2+}$, or ammonium cations, for example $NH_4^+$, $HN(CH_3)_3^+$, $N(CH_3)_4^+$, $N(C_2H_5)_4^+$, $HN(C_2H_5)_3^+$, $(DBU—H)^+$ or mixtures of these cations.

The method of the reaction of the sulfochloride (III) with cyanates, for example sodium cyanate or potassium cyanate, and heterocyclic amines (VIII) to give compounds (VII) (variant 2c) is described in principle in the abovementioned literature; see, for example, German Patent Application P 4415049.0 (WO 95/29899). The subsequent reduction of the nitro group can be carried out, as in the case of the compound (IV), in accordance with customary methods, for example preferably by catalytic reduction as already described above for compounds (VII).

In the 3rd stage, the compounds (I') obtained from the second stage, of the formula (I) in which A is H, can be acylated to give herbicidal active ingredients (I') of the formula (I) in which A is an acyl radical. Surprisingly, acylation takes place very selectively at the amino group attached to the phenyl ring using customary acylating agents. Acylation is accomplished, for example, in an aprotic organic solvent and can be carried out using customary acylating reagents. Examples of acylating agents are anhydrides, carbonyl halides, activated esters (=active esters), such as carbonic esters and chlorocarbonic esters, sulfonyl chlorides, etc. For example, a range of very good standard techniques is available for the formylation of the amino function of sulfonylureas (I') of the formula (I) in which A is H. Thus, the amino function can be converted into the formylamino group using mixed anhydrides of the formula (XII).

H—CO—O—CO—R     (XII)

R=alkyl or using formic acid.

Mixed anhydrides can be prepared by methods known from the literature, from formic acid and from carboxylic anhydrides, for example acetic anhydride, or from salts of formic acid, for example sodium formate, and carbonyl chlorides, for example acetyl chloride or pivaloyl chloride.

The individual intermediates of the novel process are novel and the invention likewise relates to them.

The individual reaction stages of the overall process described can be carried out in homogenous solution or else in supersaturated, i.e. kinetically stable, solution or in heterogeneous suspension in order, in each case, to obtain advantageous space-time yields. In such procedures, very good yields and purities are generally obtained. By a skillful combination of the individual stages it is possible to obtain overall yields of sulfonylureas of the formula (I), preferably those having the acylamino function para to the carboxamido group, which are superior to the yields described in the literature (DE 4415049, WO 95/29899).

By a skillful choice of reaction conditions it is possible, moreover, to combine two or more stages to form one-pot reactions or cascade reactions. By this means it is possible in some cases to make considerable improvements in both the yield and the space-time yield.

Preference is given to the preparation of compounds of the formula (I) in which n is 0, $R^3$ is H and the amino group on the phenyl radical is para to the carboxamido group and meta to the $SO_2$ function (=compounds (Ia)).

Particular preference is attached to the novel process and its component stages wherein a compound of the formula (IIa)

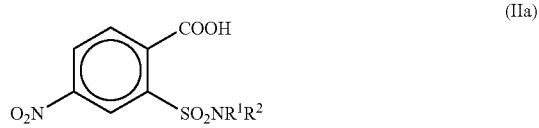

in which $R^1$ and $R^2$ are as defined for formula (I) is reacted in the presence of a halogenating agent, with the formation of acid halide and with rearrangement, to form the compound of the formula (IIIa),

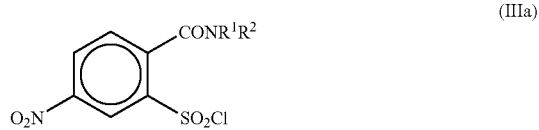

which is then converted with ammonia to the amide of the formula (IVa)

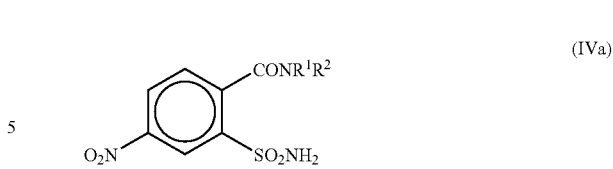

which is then reduced at the nitro group to form the compound (Va),

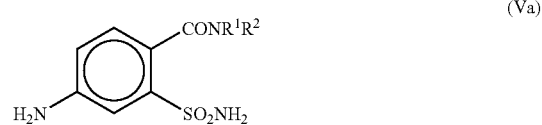

which in turn is reacted with carbamate salt of the formula (VIa)

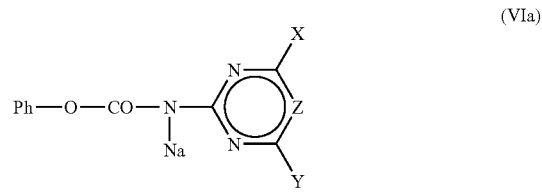

to give the compound (Ia).

In the Preparation Examples below, quantities and percentages are by weight unless stated otherwise. "m.p." denotes melting point.

PREPARATION EXAMPLES

Example 1

2-Dimethylaminocarbonyl-5-nitrobenzenesulfonyl chloride 40 ml of thionyl chloride are added to a suspension of 195.2 g of N,N-dimethyl-2-carboxy-5-nitrobenzenesulfonamide in 800 ml of chlorobenzene. The mixture is then heated slowly to 70–75° C. with vigorous stirring. Following the addition of a further 120 ml of thionyl chloride, the reaction mixture is heated at boiling. After the end of the reaction, the reaction mixture is concentrated under reduced pressure, to give 209 g of the desired product, which is sufficiently pure for subsequent reactions; m.p.: 129–131° C.

Example 2

2-Dimethylaminocarbonyl-5-nitrobenzenesulfonamide 37 ml of concentrated ammonia solution (33% strength) are added dropwise at 5° C. and with stirring to a mixture of 77.8 g of 2-dimethylaminocarbonyl-5-nitrobenzenesulfonyl: chloride and 780 ml of tetrahydrofuran. The mixture is subsequently stirred until the end of the reaction. The reaction mixture is concentrated under reduced pressure and the residue is stirred with a little water. Drying gives 66.9 g of the desired product.

m.p.: 159–160° C.

Example 3

5-Amino-2-dimethylaminocarbonylbenzenesulfonamide 1 g of moist Raney nickel is added to a solution of 12.5 g of 2-dimethylaminocarbonyl-5-nitrobenzenesulfonamide in 250 ml of methanol, and thorough mixing is carried out at 60° C. under a hydrogen pressure of 50 bar. After the end of uptake of hydrogen, the catalyst is separated off and the filtrate is concentrated, giving 11.0 g of desired product.

Example 4

5-Amino-2-dimethylaminocarbonyl-N-[(4,6-dimethoxypyrimidin-2-yl)-aminocarbonyl]benzenesulfonamide Method A:

128.4 g of 4,6-dimethoxy-2-phenoxycarbonylamino)pyrimidine are placed at 0° C. in 1250 ml of THF (tetrahydrofuran). Following the addition of 44.8 g of sodium tert-butylate, this solution is added dropwise at 0-2° C. to a mixture of 108.1 g of 5-amino-2-dimethylaminocarbonyl-benzenesulfonamide in 1250 ml of THF. After the end of reaction, the reaction mixture is concentrated. The residue is partitioned between 1500 ml of water and 780 ml of petroleum ether, and is carefully acidified with concentrated hydrochloric acid (100 ml). The precipitated solid is washed with petroleum ether and ethyl acetate. Drying gives 186.9 g of the desired product. m.p.: 192–193° C. with decomposition.

Method B:
a) 5.3 g of 2-amino-4,6-dimethoxypyrimidine and 10 g of 2-dimethylaminocarbonyl-5-nitrobenzenesulfonyl chloride are added in succession to a suspension of 3.78 g of sodium cyanate, 4.7 ml of pyridine and 100 ml of acetonitrile. The mixture is subsequently stirred at room temperature until reaction is complete, and then introduced into dilute, cooled, hydrochloric acid. The crude product obtained is purified by column chromatography ($CH_2Cl_2CH_3OH$=95:5), giving 3.1 g of the desired product; m.p.: 182–186° C. with decomposition.
b) 14 g of 2-dimethylaminocarbonyl-5-nitro-N-[(4,6-dimethoxypyrimidin-2-yl)aminocarbonyl]benzenesulfonamide are suspended in 25 ml of water, and 5.5 ml of 1 N sodium hydroxide solution are added. Following the addition of 0.1 g of 10% palladium on charcoal (50% water), the mixture is stirred vigorously at room temperature under a hydrogen atmosphere (1 bar). After the end of reaction, the catalyst is separated off by filtration and washed with a little water. Acidification of the aqueous phase with concentrated hydrochloric acid gives 1.1 g of the desired product; m.p.: 192–193° C. with decomposition.

Example 5

N,N-Dimethyl-2-methoxycarbonyl-5-nitrobenzenesulfonamide 250.6 g of potassium carbonate are added at 5° C. and with vigorous stirring to a mixture of 202.8 g of 2-methoxycarbonyl-5-nitrobenzenesulfochloride and 65.1 g of dimethylamine hydrochloride in 1000 ml of acetonitrile. After the end of reaction, the solid is separated off by filtration and washed with ethyl acetate. The combined organic phases are subsequently concentrated under reduced pressure, to give 206.7 g of the desired product. m.p.: 93–96° C.

Example 6

N,N-Dimethyl-2-carboxy-5-nitrobenzenesulfonamide 60.2 g of lithium hydroxide monohydrate are added to a solution of 206.7 g of N,N-dimethyl-2-methoxycarbonyl-5-nitrobenzenesulfonamide in 1500 ml of methanol. The mixture is subsequently stirred at 50° C. until conversion is complete. Following the concentration of the reaction mixture under reduced pressure, the residue is taken up in water and is treated at 0° C. with concentrated hydrochloric acid (pH=1). Filtration with suction followed by drying gives the desired compound. Yield: 162.9 g; m.p.: 160–163° C.

Example 7

2-Dimethylaminocarbonyl-5-nitro-N4-[(4,6-dimethoxypyrimidin-2-yl)aminocarbonyl]benzenesulfonamide Method 1:

31.7 g of 4,6-dimethoxy-2-phenoxycarbonylamino)pyrimidine are placed at 0° C. in 400 ml of THF. Following the addition of 11.08 g of sodium tert-butylate, this solution is added dropwise at 0° C. to a mixture of 30.0 g of 2-dimethylaminocarbonyl-5-nitrobenzenesulfonamide in 400 ml of THF. After the end of reaction, the reaction mixture is concentrated, partitioned between 500 ml of water and 250 ml of petroleum ether, and acidified with concentrated hydrochloric acid. The solid obtained is washed with petroleum ether and ethyl acetate. Drying gives 43.4 g of the desired product, m.p.: 182–186° C. with decomposition.

Method 2:

18.6 ml of 1 N sodium hydroxide solution are added dropwise, at room temperature and with vigorous stirring, to a suspension of 5.0 g of 2-dimethylaminocarbonyl-5-nitrobenzenesulfonamide in 20 ml of water. Subsequently, 5.04 g of 4,6-dimethoxy-2-phenoxycarbonylaminopyrimidine are added. The reaction mixture is heated to about 506° C. and stirred at this temperature until conversion is complete. The aqueous phase is then washed with diisopropyl ether and acidified with concentrated hydrochloric acid (pH=2 to 3). The precipitated solid is separated off, washed with water and dried, to give 7.6 g of desired product, whose purity is sufficient for further reactions.

Example 8

N[(4,6-Dimethoxypyrimidin-2-yl)aminocarbonyl]2-dimethylaminocarbonyl-5-acetylaminobenzenesulfonamide 0.13 ml of acetyl chloride is slowly added dropwise to a mixture of 0.64 g of N4-[(4,6-dimethoxypyrimidin-2-yl)aminocarbonyl]-5-amino-2-dimethylaminocarbonylbenzenesulfonamide and 10 ml of dimethylacetamide. After the end of reaction, the reaction mixture is concentrated under reduced pressure and the residue is washed with water and ethyl acetate, to give 0.45 g of the desired product in high purity (>92%, HPLC).

Example 9

N-[(4,6-Dimethoxypyrimidin-2-yl)aminocarbonyl]-5-formylamino-2-dimethylaminocarbonylbenzenesulfonamide A solution of 1.9 g of N-[(4,6-dimethoxypyrimidin-2-yl)aminocarbonyl]-5-amino-2-dimethylaminocarbonylbenzenesulfonamide and 10 ml of dichloromethane is added dropwise to the mixed anhydride, prepared in situ from 0.5 ml of formic acid and 1.0 ml of acetic anhydride in accordance with standard methods. After the end of reaction, the reaction mixture is concentrated and the residue is washed with water and ethyl acetate, to give 1.8 g of desired product; purity >92% (HPLC).

Example 10

N-[(4,6-Dimethoxypyrimidin-2-yl)aminocarbonyl]-2-dimethylaminocarbonyl-5-propionylaminobenzenesulfonamide 0.13 ml of propionyl chloride is added slowly dropwise to a solution of 0.64 g of 5-amino-N-[(4,6-dimethoxypyrimidin-2-yl)aminocarbonyl]-2-dimethylaminocarbonylbenzenesulfonamide in 10 ml of dimethylacetamide. After the end of reaction, the reaction mixture is concentrated under reduced pressure and the residue is washed with water and ethyl acetate, to give 0.45 g of the desired product in high purity (>92%, HPLC).

Example 11 (Comparison Example)

5-Amino-2-dimethylaminocarbonyl-N4-[(4,6-dimethoxypyrimidin-2-yl)-aminocarbonyl]benzenesulfonamide 0.6 ml of 1,8-diazabicyclo[5.4.0]undec-7-ene (DBU) is added with stirring at 0° C. to a suspension of 1.0 g of 5-amino-2-dimethylaminocarbonylbenzene-sulfonamide and 1.1 g of 4,6-dimethoxy-2-(phenoxycarbonylamino)pyrimidine in 10 ml of acetonitrile. The mixture is stirred again until complete reaction has taken place. Following the distillative removal of the volatile components, the residue is taken up in a little water and washed with diethyl ether. The aqueous phase is subsequently acidified With concentrated hydrochloric acid (pH=2–3). The deposited solid is washed with diisopropyl ether and then dried, to give 1.4 g of a solid which comprises the two compounds 5-amino-2-dimethylaminocarbonyl-N-[(4,6-dimethoxypyrimidin-2-yl)-aminocarbonyl]-benzenesulfonamide and 5-[(4,6-dimethoxypyrimidin-2-yl)aminocarbonylamino]-2-dimethylaminocarbonyl-N-[(4,6-dimethoxypyrimidin-2-yl)aminocarbonyl]benzenesulfonamide in a ratio of about 2:1.

The invention claimed is:

1. A compound of formula (VII) or salt thereof:

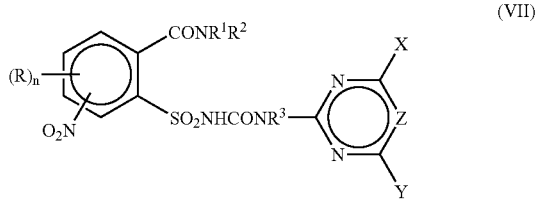

(VII)

wherein (R)$_n$ is n identical or different radicals from the group consisting of halogen, alkyl and alkoxy, n is 0 or 1, R$^1$ is H, C$_1$–C$_6$-alkyl, C$_2$–C$_6$-alkenyl, C$_2$–C$_6$-alkynyl, C$_1$–C$_6$-alkoxy, C$_2$–C$_6$-alkenoxy, C$_2$–C$_6$-alkynoxy or C$_5$–C$_6$-cycloalkyl, each of the 7 latter radicals being unsubstituted or substituted by one or more radicals from the group consisting of halogen, C$_1$–C$_4$-alkoxy, C$_1$–C$_4$-haloalkoxy, C$_1$–C$_4$-alkylthio, mono- and di-(C$_1$–C$_4$-alkyl)-amino, cyano, azido, formyl, (C$_1$–C$_4$-alkyl)-carbonyl, (C$_1$–C$_4$-alkoxy)-carbonyl, C$_1$–C$_4$-alkylsulfinyl and C$_1$–C$_4$-alkylsulfonyl, or is phenyl which is unsubstituted or substituted by radicals from the group consisting of halogen, C$_1$–C$_4$-alkyl, C$_1$–C$_4$-alkoxy, C$_1$–C$_4$-hatoalkyl, C$_1$–C$_4$-haloalkoxy and nitro, R$^2$ is H, C$_2$–C$_6$-alkyl, C$_2$–C$_6$-alkenyl or C$_2$–C$_6$-alkynyl, each of the three latter radicals being unsubstituted or substituted by one or more radicals from the group consisting of halogen, C$_1$–C$_4$-alkoxy, C$_1$–C$_4$-haloalkoxy, C$_1$–C$_4$-alkylthio, mono- and di-(C$_1$–C$_4$-alkyl)-amino, cyano, azido, formyl, (C$_1$–C$_4$-alkyl)-carbonyl, (C$_1$–C$_4$-alkoxy)-carbonyl, C$_1$–C$_4$-alkylsulfinyl and C$_1$–C$_4$-alkylsulfonyl, or the group NR$^1$R$^2$ is a heterocyclic ring of 4, 5 or 6 ring atoms which may contain up to two further ring heteroatoms from the group consisting of N and O in the ring and which is unsubstituted or substituted by one or more radicals from the group consisting of C$_1$–C$_4$-alkyl, R$^3$ is hydrogen or methyl, X and Y independently of one another are halogen, C$_1$–C$_6$-alkyl, C$_1$–C$_6$-alkoxy, C$_1$–C$_6$-alkylthio, each of the three latter radicals being unsubstituted or substituted by one or more radicals from the group consisting of halogen, C$_1$–C$_4$-alkoxy and C$_1$–C$_4$-alkylthio, or are C$_3$–C$_6$-cycloalkyl, C$_2$–C$_6$-alkenyl, C$_2$–C$_6$-alkynyl, C$_3$–C$_6$-alkenyloxy or C$_3$–C$_6$-alkynyloxy, and Z is CH.

2. The compound or salt thereof of claim 1, wherein (R)$_n$ is halogen, C$_1$–C$_4$-alkyl or C$_1$–C$_4$-alkoxy, n is 0 or 1, R$^1$ is H, C$_1$–C$_6$-alkyl, C$_2$–C$_6$-alkenyl, C$_2$–C$_6$-alkynyl, C$_1$–C$_6$-alkoxy, C$_2$–C$_6$-alkenoxy, C$_2$–C$_6$-alkynoxy or C$_5$–C$_6$-cycloalkyl, each of the 7 latter radicals being unsubstituted or substituted by one or more radicals from the group consisting of halogen, C$_1$–C$_4$-alkoxy, C$_1$–C$_4$-haloalkoxy, C$_1$–C$_4$-alkylthio, mono- and di-(C$_1$–C$_4$-alkyl)-amino, cyano, azido, formyl, (C$_1$–C$_4$-alkyl)-carbonyl, (Ci -C$_4$-alkoxy)-carbonyl, C$_1$–C$_4$-alkylsulfinyl and C$_1$–C$_4$-alkylsulfonyl, or is phenyl which is unsubstituted or substituted by radicals from the group consisting of halogen, C$_1$–C$_4$-alkyl, C$_1$–C$_4$-alkoxy, C$_1$–C$_4$-haloalkyl, C$_1$–C$_4$-haloalkoxy and nitro, R$^2$ is H, C$_2$–C$_6$-alkyl, C$_2$–C$_6$-alkenyl or C$_2$–C$_6$-alkynyl, each of the three latter radicals being unsubstituted or substituted by one or more radicals from the group consisting of halogen, C$_1$–C$_4$-alkoxy, C$_1$–C$_4$-haloalkoxy, C$_1$–C$_4$-alkylthio, mono- and di-(C$_1$–C$_4$-alkyl)-amino, cyano, azido, formyl, (C$_1$–C$_4$-alkyl )-carbonyl, (C$_1$–C$_4$-alkoxy)-carbonyl, C$_1$–C$_4$-alkylsulfinyl and C$_1$–C$_4$-alkylsulfonyl, or the group NR$^1$R$^2$ is a heterocyclic ring of 4, 5 or 6 ring atoms which may contain up to two further ring heteroatoms from the group consisting of N and O in the ring and which is unsubstituted or substituted by one or more radicals from the group consisting of C$_1$–C$_4$-alkyl, R$^3$ is H or CH$_3$, one of the radicals X and Y is halogen, $C_1$–$C_2$-alkyl, $C_1$–$C_2$-alkoxy, $C_1$–$C_2$-alkylthio, each of the three latter radicals being unsubstituted or substituted by one or more radicals from the group consisting of halogen, $C_1$–$C_2$-alkoxy and $C_1$–$C_2$-alkylthio, or is mono- or di-($C_1$–$C_2$-alkyl)amino, and the other of the radicals X and Y is $C_1$–$C_2$-alkyl, $C_1$–$C_2$-haloalkyl, $C_1$–$C_2$-alkoxy, $C_1$–$C_2$-haloalkoxy or $C_1$–$C_2$-alkylthio, Z is CH.

3. A process for preparing a compound or salt thereof of claim 1, which comprises:

(1) reacting the compound of formula (II) or salt thereof

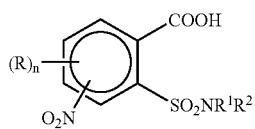

(II)

in the presence of a halogenating agent, with formation of the carbonyl halide and its rearrangement to form the compound of formula (III)

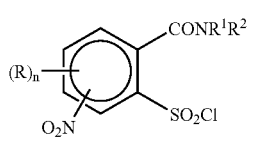

(III)

wherein $(R)_n$ is n identical or different radicals from the group consisting of halogen, alkyl and alkoxy, n is 0 or 1, $R^1$ is H, $C_1$–$C_6$-alkyl, $C_2$–$C_6$-alkenyl, $C_2$–$C_6$-alkynyl, $C_1$–$C_6$-alkoxy, $C_2$–$C_6$-alkenoxy, $C_2$–$C_6$-alkynoxy or Cs-$C_6$-cycloalkyl, each of the 7 latter radicals being unsubstituted or substituted by one or more radicals from the group consisting of halogen, $C_1$–$C_4$-alkoxy, $C_1$–$C_4$-haloalkoxy, $C_1$–$C_4$-alkylthio, mono- and di-($C_1$–$C_4$-alkyl)-amino, cyano, azido, formyl, (Ci-$C_4$-alkyl)-carbonyl, ($C_1$–$C_4$-alkoxy)-carbonyl, $C_1$–$C_4$-alkylsulfinyl and $C_1$–$C_4$-alkylsulfonyl, or is phenyl which is unsubstituted or substituted by radicals from the group consisting of halogen, $C_1$–$C_4$-alkyl, $C_1$–$C_4$-alkoxy, $C_1$–$C_4$-haloalkyl, $C_1$–$C_4$-haloalkoxy and nitro, $R^2$ is H, $C_2$–$C_6$-alkyl, $C_2$–$C_6$-alkenyl or $C_2$–$C_6$-alkynyl, each of the three latter radicals being unsubstituted or substituted by one or more radicals from the group consisting of halogen, $C_1$–$C_4$-alkoxy, $C_1$–$C_4$-haloalkoxy, $C_1$–$C_4$-alkylthio, mono- and di-($C_1$–$C_4$-alkyl)-amino, cyano, azido, formyl, ($C_1$–$C_4$-alkyl)-carbonyl, ($C_1$–$C_4$-alkoxy)-carbonyl, $C_1$–$C_4$-alkyisulfinyl and $C_1$–$C_4$-alkylsulfonyl, or the group $NR^1R^2$ is a heterocyclic ring of 4, 5 or 6 ring atoms which may contain up to two further ring heteroatoms from the group consisting of N and O in the ring and which is unsubstituted or substituted by one or more radicals from the group consisting of $C_1$–$C_4$-alkyl, (2a) reacting the compound of formula (III) to ammonolysis at the $SO_2Cl$ group to give the a compound of formula (IV)

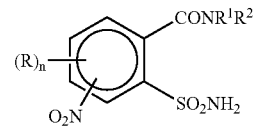

(IV)

wherein $(R)_n$, n, $R^1$ and $R^2$ is as defined above;

and then reacting the compound of formula (IV) with the compound of formula (VI)

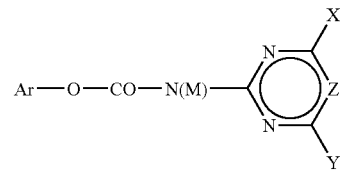

(VI)

wherein

X and Y independently of one another are halogen, $C_1$–$C_6$-alkyl, $C_1$–$C_6$-alkoxy, $C_1$–$C_6$-alkylthio, each of the three latter radicals being unsubstituted or substituted by one or more radicals from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, alkenyloxy or $C_3$–$C_6$-alkynyloxy, and Z is CH; and M is H, $C_1$–$C_4$-alkyl or a metal cation; or (2b) reacting the compound of the formula (III) with cyanates and with the heterocyclic amine of the formula (VIII)

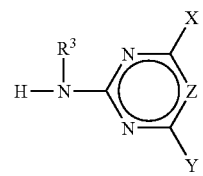

(VIII)

wherein

X and Y independently of one another are halogen, $C_1$–$C_6$-alkyl, $C_1$–$C_6$-alkoxy, $C_1$–$C_6$-alkylthio, each of the three latter radicals being unsubstituted or substituted by one or more radicals from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, and Z is CH; and $R^3$ is hydrogen or methyl.

4. The process of claim 3, wherein $(R)_n$ is halogen, $C_1$–$C_4$-alkyl or $C_1$–$C_4$-alkoxy, n is 0 or 1, $R^1$ is H, $C_1$–$C_6$-alkyl, $C_2$–$C_6$-alkenyl, $C_2$–$C_6$-alkynyl, $C_1$–$C_6$-alkoxy, $C_2$–$C_6$-alkenoxy, $C_2$–$C_6$-alkynoxy or $C_5$–$C_6$-cycloalkyl, each of the 7 latter radicals being unsubstituted or substituted by one or more radicals from the group consisting of halogen, $C_1$–$C_4$-alkoxy, $C_1$–$C_4$-haloalkoxy, $C_1$–$C_4$-alkylthio, mono- and di-($C_1$–$C_4$-alkyl)-amino, cyano, azido, formyl, ($C_1$–$C_4$-alkyl)-carbonyl, ($C_1$–$C_4$-alkoxy)-carbonyl, $C_1$–$C_4$- alkylsulfinyl and $C_1$–$C_4$-alkylsulfonyl, or is phenyl which is unsubstituted or substituted by radicals from the group consisting of halogen, $C_1$–$C_4$-alkyl, $C_1$–$C_4$-alkoxy, $C_1$–$C_4$-haloalkyl, $C_1$–$C_4$-haloalkoxy and nitro, $R^2$ is H, $C_2$–$C_6$-alkyl, $C_2$–$C_6$-alkenyl or $C_2$–$C_6$-alkynyl, each of the three latter radicals being unsubstituted or substituted by one or more radicals from the group consisting of halogen, $C_1$–$C_4$-alkoxy, $C_1$–$C_4$-haloalkoxy, $C_1$–$C_4$-alkylthio, mono- and di-($C_1$–$C_4$-alkyl)-amino, cyano, azido, formyl, ($C_1$–$C_4$-alkyl)-carbonyl, ($C_1$–$C_4$-alkoxy)-carbonyl, $C_1$–$C_4$-alkylsulfinyl and $C_1$–$C_4$-alkylsulfonyl, or the group
$NR^1R^2$ is a heterocyclic ring of 4, 5 or 6 ring atoms which may contain up to two further ring heteroatoms from the group consisting of N and O in the ring and which is unsubstituted or substituted by one or more radicals from the group consisting of $C_1$–$C_4$-alkyl, $R^3$ is H or $CH_3$, one of the radicals X and Y is halogen, $C_1$–$C_2$-alkyl, $C_1$–$C_2$-alkoxy, $C_1$–$C_2$-alkylthio, each of the three latter radicals being unsubstituted or substituted by one or more radicals from the group consisting of halogen, $C_1$–$C_2$-alkoxy and $C_1$–$C_2$-alkylthio, or is mono- or di-($C_1$–$C_2$-alkyl)amino, and the other of the radicals X and Y is $C_1$–$C_2$-alkyl, $C_1$–$C_2$-haloalkyl, $C_1$–$C_2$-alkoxy, $C_1$–$C_2$-haloalkoxy or $C_1$–$C_2$-alkylthio, Z is CH; and M is H, $C_1$–$C_4$-alkyl or a metal cation.

* * * * *